United States Patent [19]

Schnur

[11] Patent Number: 4,656,169
[45] Date of Patent: Apr. 7, 1987

[54] TETRACYCLIC SPIRO-HYDANTOIN ALDOSE REDUCTASE INHIBITORS AND COMPOSITIONS

[75] Inventor: Rodney C. Schnur, Noank, Conn.

[73] Assignee: Pfizer Inc., New York, N.Y.

[21] Appl. No.: 854,588

[22] PCT Filed: Aug. 14, 1984

[86] PCT No.: PCT/US84/01290
§ 371 Date: Apr. 10, 1986
§ 102(e) Date: Apr. 10, 1986

[87] PCT Pub. No.: WO86/01107
PCT Pub. Date: Feb. 27, 1986

[51] Int. Cl.⁴ .............. A61K 31/495; A61K 31/535; C07D 487/20

[52] U.S. Cl. .................. 514/235; 514/250; 544/70; 544/230

[58] Field of Search .............. 544/70, 230; 514/235, 514/250

[56] References Cited

U.S. PATENT DOCUMENTS

| | | |
|---|---|---|
| 3,821,383 | 6/1974 | Sestani et al. ............ 514/296 |
| 4,130,714 | 12/1978 | Sarges .................... 548/309 |
| 4,193,996 | 3/1980 | Schnur .................... 546/15 |
| 4,235,911 | 11/1980 | Sarges .................... 546/18 |

Primary Examiner—Robert W. Ramsuer
Attorney, Agent, or Firm—Charles J. Knuth; Peter C. Richardson; Mark Dryer

[57] ABSTRACT

Novel biologically-active tetracyclic spiro-hydantoin derivatives which are potent inhibitors of aldose reductase and useful in treating diabetic complications are disclosed. Pharmaceutical compositions containing the novel compounds and a method of treating chronic diabetic complications are also disclosed. A preferred compound is 9'-chloro-5',6'-dihydro-2'-phenyl-spiro[imidazolidine-5,7'-7'H-pyrido(1,2,3-de)quinoxaline]2,3',4-trione.

5 Claims, No Drawings

TETRACYCLIC SPIRO-HYDANTOIN ALDOSE REDUCTASE INHIBITORS AND COMPOSITIONS

TECHNICAL FIELD

This invention relates to novel biologically-active tetracyclic spiro-hydantoin derivatives, a process for the preparation thereof and pharmaceutical compositions containing the novel compounds.

The novel compounds of the invention are potent inhibitors of aldose reductase and are useful for the treatment of diabetic complications. Accordingly, the invention also is concerned with a method for the treatment of chronic diabetic complications.

BACKGROUND ART

In the past, various attempts have been made to obtain new and more effective oral anti-diabetic agents. Generally, these efforts have involved synthesis of new organic compounds, particular sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors, such as 1,3-dioxo-1H-benz[d,e]-isoquinoline-2(3H)-acetic acid and derivatives thereof, to be useful for the treatment of these conditions. Such aldose reductase inhibitors function by inhibiting the activity of the enzyme aldose reductase, which is primarily responsible for regulating the reduction of aldoses such as glucose and galactose to the corresponding polyols, such as sorbitol and galactitol, in humans and other animals. In this way, unwanted accumulations of galactitol in the lens of galactosemic subjects and of sorbitol in the lens, peripheral nervous cord and kidney of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

U.S. Pat. No. 4,130,714 discloses certain dextrorotatory spiro-hydantoin compounds which are extremely useful when employed in therapy as aldose reductase inhibitors for the control of chronic complications arising in a diabetic subject. The said compounds are dextrorotatory forms of asymmetric spiro-hydantoins of the formula:

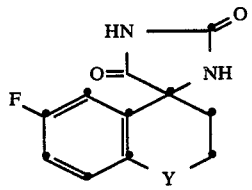

and the base salts thereof with pharmacologically acceptable cations, wherein Y is oxygen or sulfur. Typical compounds disclosed in U.S. Pat. No. 4,130,714 include d-6-fluoro-spiro-[chroman-4,4'-imidazolidine]-2',5'-dione and d-6'-fluoro-spiro[imidazolidine-4,4'-thiochroman]-2,5-dione, respectively. These two particular compounds are both extremely potent as regards their aldose reductase inhibitory activity, in addition to being equally effective in lowering sorbitol levels in the sciatic nerve and lens of diabetic subjects and galactitol levels in the lens of galactosemic subjects to a very significantly high degree.

U.S. Pat. No, 4,193,996 also discloses spiroquinolone hydantoins which are aldose reductase inhibitors useful as therapeutic agents for preventing or alleviating chronic diabetic complications. Said hydantoin compounds are of the formula:

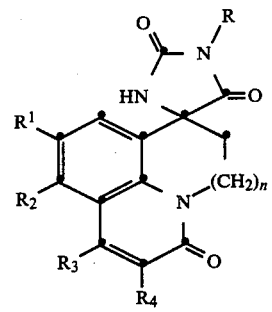

and the pharmaceutically acceptable addition salts thereof, wherein n is one or two; R, $R_3$ and $R_4$ are each hydrogen; and $R_1$ and $R_2$ are each selected from the group consisting of hydrogen, chloro, bromo, fluoro, alkyl of 1 to 3 carbon atoms and alkoxy of 1 to 3 carbon atoms.

U.S. Pat. No. 4,235,911 disclosed certain tetrahydroquinoline spiro-hydantoin compounds which also are useful when employed in therapy as aldose reductase inhibitors for the control of certain chronic complications arising in a diabetic subject. These compounds are of the formula:

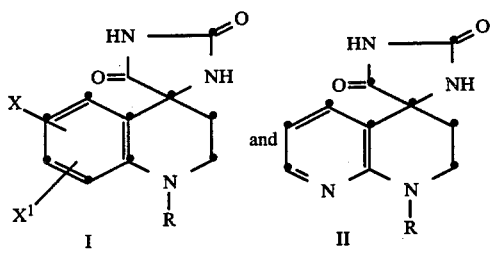

and the pharmaceutically acceptable acid addition salts thereof, wherein X is hydrogen and $X^1$ is hydrogen, lower alkoxy, fluorine, chlorine, bromine or phenyl; X and $X^1$, when taken separately, are each lower alkoxy, chlorine or phenyl, and when taken together are —$OCH_2(CH_2)_nO$— wherein n is zero or one, and R is hydrogen or lower alkyl, with the proviso that R is always other than hydrogen when $X^1$ is hydrogen. It has now been found that certain novel tetracyclic spirohydantoin derivatives are very potent inhibitors of aldose reductase and are useful in treating diabetic complications.

DISCLOSURE OF INVENTION

In accordance with the present invention there is provided a biologically-active tetracyclic spiro hydantoin derivative having the general formula:

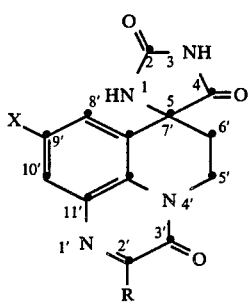

(I)

and the pharmaceutically-acceptable acid addition salts thereof; wherein

X is hydrogen, fluorine, chlorine or methyl; and R is hydrogen, $(C_1-C_9)$alkyl, $(C_2-C_9)$alkenyl, $(C_5-C_7)$cycloalkyl, benzyl, 4-hydroxybenzyl, pyridyl, $HSCH_2-$, $CH_3SCH_2-$, $CH_3SCH_2CH_2-$, $FCH_2-$, $HOCH_2-$, $CH_3CH(OH)-$, $CH_3CH(OH)CH_2-$, $HOOCCH_2-$, $HOOCCH_2CH_2-$, $H_2NCOCH_2-$, $H_2NCOCH_2CH_2-$, $H_2NCH_2CH_2CH_2CH_2-$,

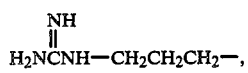

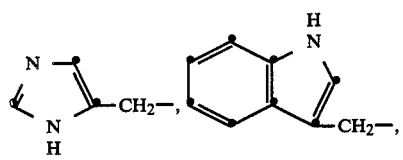

—COOC$_2$H$_5$, —CONH$_2$, —CONH(CH$_2$)$_2$OH, —CONH cyclohexyl, —CONH—nBu, —CONH(CH$_2$)$_3$N(CH$_3$)$_2$, —CON(C$_2$H$_5$)$_2$,

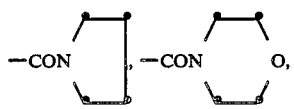

phenyl or substituted phenyl wherein the substituent is chlorine, fluorine, bromine, hydroxy, methyl, methoxy, trifluoromethyl, —COCH$_3$, —N(CH$_3$)$_2$, —SCH$_3$, —SOCH$_3$, —SO$_2$CH$_3$, —COOH, —CONH$_2$, —COOCH$_3$ or —CON Alk, wherein Alk is lower alkyl having 1 to 6 carbon atoms.

Particularly preferred compounds are those of formula (I) wherein X is chlorine.

The invention also provides a pharmaceutical composition for the treatment of diabetes complications comprising a pharmaceutically-effective amount of a compound of formula (I) in admixture with a pharmaceutically-acceptable carrier.

The invention further provides a method for the treatment of diabetes complications in a host which comprises administering to said host a pharmaceutically effective amount of a compound of formula (I).

An especially preferred compound according to the invention is 9'-chloro-5',6'-dihydro-2'-phenyl-spiro[imidazolidine-5,7'-7'H-pyrido-(1,2,3-de)quinoxaline]2,3',4-trione; i.e. the compound of formula I wherein X is chlorine and R is phenyl.

A preferred group of compounds provided by the invention is that wherein X is chlorine and R is derived drom the side chain of a naturally-occuring amino acid, particularly one the nine essential amino acids. These compounds may be represented by the general formula R.CH(NH$_2$)COOH wherein R represents the side chain of an essential amino acid as follows:

| | R | |
|---|---|---|
| Leucine: | (CH$_3$)$_2$CHCH$_2$— | (isobutyl) |
| Valine: | (CH$_3$)$_2$CH— | (isopropyl) |
| Isoleucine: | CH$_3$CH$_2$CH— <br>           \|<br>          CH$_3$ | (sec-butyl) |
| Phenylalanine: | C$_6$H$_5$CH$_2$— | (benzyl) |
| Methionine: | CH$_3$SCH$_2$CH$_2$— | (2-methylthioethyl) |
| Arginine | $\begin{array}{c}HN\\\|\|\\H_2N-CNHCH_2CH_2CH_2-\end{array}$ | |
| Histidine |  | |
| Threonine | CH$_3$CH(OH)— | |
| Tryptophan | | |

The first three of the above compounds fall into the preferred class of compounds wherein R is (C$_1$-C$_9$) alkyl; and other preferred compounds within this class are those wherein R is methyl, ethyl, n-propyl, n-butyl, hexyl or heptyl.

Other naturally-occurring amino acids whose side chains are derivative for the group R in the compounds of the invention are the following non-essential amino acids:

| | R |
|---|---|
| glycine | H |
| aspartic acid | HOOCCH$_2$— |
| glutamic acid | HOOCCH$_2$CH$_2$— |
| serine | HOCH$_2$— |
| tyrosine | HO—⟨⟩—CH$_2$— |
| cysteine | HSCH$_2$— |

Other preferred compounds provided by the invention are those of formula I wherein X is chlorine and R is 4-pyridyl, 3-pyridyl, ethoxycarbonyl or fluoromethyl.

A still further group of preferred compounds is that of formula I wherein X is chlorine and R is —CONR$^1$R$^2$ wherein R$^1$ and R$^2$ are both hydrogen or ethyl or R$^1$ is hydrogen and R$^2$ is n-butyl, cyclohexyl, dimethylaminopropyl or 2-hydroxyethyl; or R$^1$ and R$^2$ together with the nitrogen atom to which they are attached form a pyrrolidino or morpholino ring.

The compounds of formula I wherein R is other than a carboxamido group of the formula —CONR$^1$R$^2$ may be prepared by a process which comprises reacting an intermediate amine having the formula:

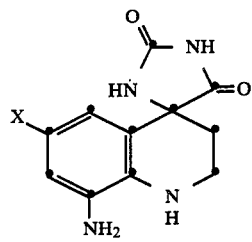

(II)

wherein X is hydrogen, fluorine, chlorine or methyl, preferably chlorine, with an α-keto acid, ester or salt of the formula:

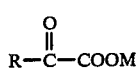

(III)

wherein R is as defined above, other than —CONR$^1$R$^2$, and M is hydrogen, (C$_1$-C$_4$)alkyl or an alkali metal, in the presence of an acid catalyst. The preferred ester is the ethyl ester and the preferred alkali metal salt is the sodium salt.

The compounds of formula I wherein R is a carboxamido group of the formula —CONR$^1$R$^2$, wherein R$^1$ and R$^2$ are as defined above, may be prepared by a process which comprises reacting a compound of formula (I) wherein R is ethoxycarbonyl, i.e. the compound of the formula:

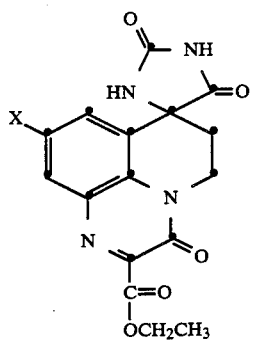

(I')

wherein X is as defined above, with an appropriate amine of the formula HNR$^1$R$^2$, wherein R$^1$ and R$^2$ are as defined above.

DETAILED DESCRIPTION

The intermediate amine of formula (II) above may be prepared by a series of steps from certain hydantoin starting compounds whose preparation is described in U.S. Pat. No. 4,235,911 and the full sequence of steps leading from said starting compounds to the compounds of formula (I), wherein X is chlorine and R is other than —CONR$^1$R$^2$, is illustrated in the following reaction Scheme A:

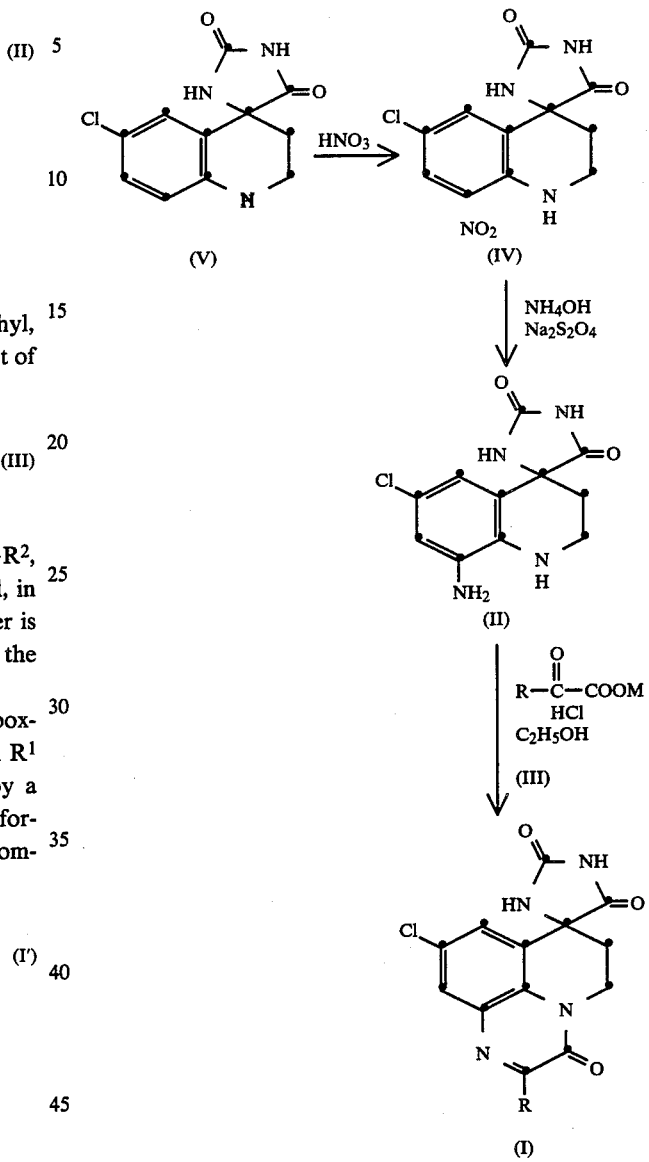

In the procedure illustrated in Reaction Scheme A the starting hydantoin compound of formula (V) is 6'-chloro-1',2',3',4'-tetrahydro-spiro(imidazolidine-5,4'-quinoline)2,4-dione which may be prepared by the process described in U.S. Pat. No. 4,235,911.

In the first step of the procedure the starting compound of formula (V) is reacted with concentrated nitric acid to form the 8'-nitro derivative of formula (IV).

The compound of formula (IV) is then reacted with concentrated ammonium hydroxide in the presence of sodium dithionite (Na$_2$S$_2$O$_4$) to provide the 8'-amino derivative of formula (II).

The intermediate of formula (II) is then reacted, in accordance with the process of the invention, with an (R-substituted)-α-keto acid, ester or salt of formula (III), in the presence of an acid catalyst, to form the desired product of formula (I). The preferred acid used in the acid catalysis is concentrated hydrochloric acid, which is preferably used with ethanol as illustrated in the Reaction Scheme. Another suitable acid is glacial acetic acid and this acid is particularly suitable when the intermediate of formula (III) is in the form of the sodium salt.

The compounds of formula (I) wherein R is —CONR$^1$R$^2$ and X is chlorine are prepared by the process illustrated in the following Reaction Scheme B:

REACTION SCHEME B

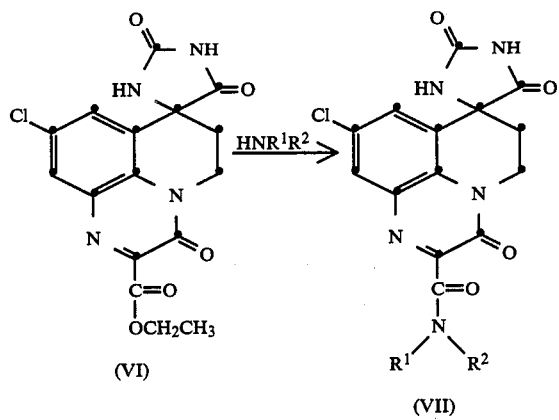

(VI)

(VII)

In the procedure illustrated in Reaction Scheme B 9'-chloro-5',6'-dihydro-spiro[imidazolidine-5,7'-7'H-pyrido(1,2,3-de)quinoxaline]-2,3',4-trione-2'-carboxylic acid ethyl ester of formula (VI), which alternatively may be designated as 9'-chloro-5',6'-dihydro-2'-ethoxycarbonyl-spiro[imidazolidine-5,7'-7'H-pyrido(1,2,3-de)quinoxaline]-2,3',4-trione, is reacted with an appropriate amine of the formula HNR$^1$R$^2$, wherein R$^1$ and R$^2$ are as defined above to provide the desired carboxamido product of formula (VII).

Pharmaceutically-acceptable acid addition salts of the compounds of formula I may be readily prepared by conventional methods. Thus these acid addition salts may be prepared by reacting the base form of the compound with an appropriate mineral or organic acid which forms a non-toxic acid addition salt having a pharmacologically-acceptable anion, such as the hydrochloride, hydrobromide, hydroiodide, sulfate of bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate or p-toluenesulfonate salt. For instance, the salt-formation step may be carried out by using a substantially equimolar amount of the appropriate acid in an aqueous solvent medium or in a suitable organic solvent such as methanol or ethanol. Upon careful evaporation of the solvent, the solid salt is readily obtained.

It will be understood that the novel spiro-hydantoin derivatives of this invention contain an asymmertric center and thus will exhibit optical isomerism. If desired, the racemic spiro-hydantoin formed by the methods previously described may be resolved into the d- and l-isomeric forms by the application of conventional resolution methods. For example, adducts of one isomer with, for example, cinchonidine, brucine, or l-amphetamine, may be formed and the free isomer obtained from such adducts by hydrolysis with aqueous acid. The other isomer may be recovered from the mother liquor after removal of the adduct described above.

The novel tetracyclic spiro hydantoin derivatives of formula (I) are useful as aldose reductase inhibitors, and as such are of therapeutic value in the treatment of chronic complications of diabetes, such as cataracts, retinopathy and neuropathy. As used herein, treatment is meant to include both prevention or alleviation of such conditions. The compounds may be administered to a subject in need of treatment by a variety of conventional routes of administration, including orally, parenterally and topically. In general, these compounds will be administered at dosages between about 1 and 250 mg/kg body weight of the subject to be treated per day. However, some variation in dosage will necessarily occur depending on the condition of the subject being treated and the person responsible for administration will, in any event, determine the appropriate dose for the individual subject.

The compounds may be administered alone or in combination with pharmaceutically-acceptable carriers, in either single or multiple doses. Suitable pharmaceutical carriers include inert solid diluents or fillers, sterile aqueous solutions and various organic solvents. The pharmaceutical compositions formed by combining the novel compounds of formula I and the pharmaceutically-acceptable carriers are then readily administered in a variety of dosage forms such as tablets, powders, lozenges, syrups or injectable solutions. These pharmaceutical compositions, if desired, may contain additional ingredients such as flavoring, binders or excipients. Thus, for purposes or oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin or combinations thereof.

For parenteral administration, solutions of the compounds of formula (I) in sesame oil or peanut oil or in aqueous propylene glycol may be employed, as well as sterile aqueous solutions of the water-soluble salts. Such aqueous solutions should be suitably buffered, if necessary, and the liquid diluent first rendered isotonic with sufficient saline or glucose. These particular aqueous solutions are especially suitable for intraveneous, intramuscular, subcutaneous and intraperitoneal administration. In this connection, the sterile aqueous media employed are all readily available by standard techniques known to those skilled in the art. Additionally, it is also possible to administer the tetracyclic spiro hydantoin derivatives topically, by use of an appropriate ophthalmic solution which may then be administered drop-wise to the eye.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized (i.e. diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats; and (5) measuring their ability to delay cataract formation and reduce the severity of lens opacities in chronic galactosemic rats.

The following Examples illustrate the preparation of preferred compounds according to the invention.

EXAMPLE 1

(a) Preparation of 6'-chloro-8'-nitro-1',2',3',4'-tetrahydro-spiro[imidazolidine-5,4'-quinoline]-2,4-dione (formula IV)

5.00 g. (0.0199 mol) of 6'-chloro-1',2',3',4'-tetrahydro-spiro(imidazolidine-5,4'-quinoline)-2,4-dione, formula (V), prepared as described in U.S. Pat. No. 4,235,911, was added to 500 ml of concentrated nitric acid precooled to 7° C. measured internally. After one minute the reaction mixture was poured into 4 liters of ice water and extracted with 2×1 liter of ethyl acetate. The combined organic layers were washed with 1 liter of water, dried over magnesium sulfate, filtered and concentrated to a yellow solid. The solid was slurried in ether/hexane (⅓) filtered and dried in vacuo to provide 5.8 g. (98%) of the title product, m.p. 271° to 274° C. dec.

(b) Preparation of 8'-amino-6'-chloro-1',2',3',4'-tetrahydro-spiro[imidazolidine-5,4'-quinoline]-2,4-dione (formula II)

7.0 g. (0.024 mol) of the 8'-nitro derivative of formula (IV) prepared in step (a) was suspended in a mixture of 80 ml. of water and 40 ml. of concentrated ammonium hydroxide, heated at a temperature of 90° C. and reacted with 18.15 g. (0.113 mol) of sodium thionite ($Na_2S_2O_4$), added in 2 g. portions every two minutes.

After thirty minutes the reaction mixture was cooled, concentrated to half volume in vacuo and adjusted to pH 7 with 1N hydrochloric acid. The resultant solid particles were filtered, washed with water, and dried in vacuo overnight at 60° C. to provide 3.92 g. (61%) of the title product, m.p. 250° to 253° C. dec.

(c) Preparation of 9'-chloro-5',6'-dihydro-2'-phenyl-spiro[imidazolidine-5,7'-7'H-pyrido-(1,2,3-de)quinoxaline]-2,3',4-trione (formula I)

0.19 g. (0.71 mmol) of the 8'-amino derivative of formula (II) prepared in step (b) was added to a solution comprising 0.15 g. (1.0 mmol) of phenylglyoxylic acid, formula III, and 1.50 ml (18 mmol) of concentrated hydrochloric acid in 6 ml. of ethanol and the mixture was stirred at room temperature of one hour.

The resulting precipitate was filtered, washed with ethanol and ether and air-dried. This provided 192.0 mg. (71%) of the title product, m.p. 285.5° to 289.0° C.

Analysis: Calc. for $C_{19}H_{13}O_3N_4Cl(0.5H_2O)$: C-58.54; H-3.62; N-14.37%. Found: C-58.55; H-3.71; N-14.34%.

EXAMPLE 2

Example 2

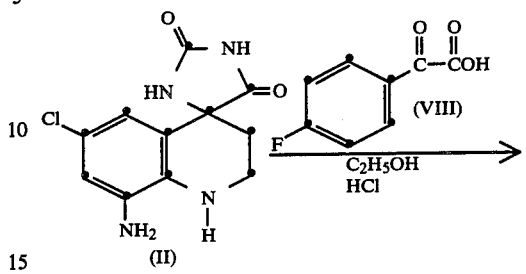

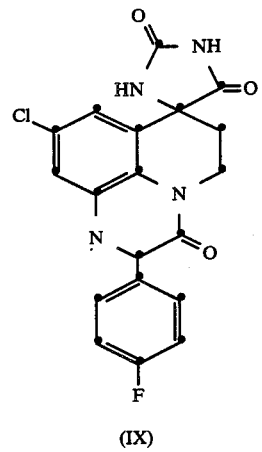

(a) Preparation of 4-fluorophenyl glyoxylic acid (formula VIII)

2.01 g. (10.29 mmol) of 5-(4-fluorophenyl)oxazolidine-2,3-dione, prepared as described in U.S. Pat. No. 4,367,234, was hydrolyzed in 12 ml of absolute ethanol with 6N NaOH (1.0 ml) for 2 hours at reflux. The reaction mixture was concentrated to a white powder and partitioned between ethyl acetate and water. The water layer was acidified with 1N hydrochloric acid and extracted with 2×20 ml ethyl acetate. The latter organic phases were pooled, washed with 30 ml brine, dried ($MgSO_4$), filtered and concentrated in vacuo to a white solid; 1.70 g. (97%) m.p. 124° to 125° C. The fluoro mandelic acid was esterified in 20 ml absolute ethanol with 1 ml concentrated sulfuric acid as catalyst for 18 hours at 40° C. Neutralization of this reaction mixture with sodium bicarbonate and extraction with ethyl acetate (150 ml) yielded the ester as a fine white powder after vacuum evaporation m.p. 44° to 47° C. 1.00 g. of this ethyl p-fluoro mandelate (5.046 mmoles) was stirred in 1 ml. of water as a solution of 220 mg. of sodium hydroxide in 1 ml. of water was added. After this mixture become homogeneous it was cooled to 0° C. and 550 mg. (3.48 mmol) of finely ground potassium permanganate was added. After 1½ hours the purple suspension was filtered through Celite and the filter cake washed with 25 ml water. The combined aqueous phases were acidified with 1N hydrochloric acid and a fine white crystalline solid precipitated; 0.71 g. (89%) m.p. 67° C. This sample of 4-fluorophenylglyoxylic acid was shown to be contaminated with approximately 10% of p-fluoro mandelic acid but was used without further purification. (A more optimum procedure for the preparation may eliminate the esterification step).

(b) Preparation of 9'-chloro-5',6'-dihydro-2'-(4-fluorophenyl)-spiro[imidazoline-5,7'-7'H-pyrido(1,2,3-de)quinoxaline]-2,3',4-trione (formula IX)

266.3 mg. (0.998 mmol) of the 8'-amino derivative of formula (II) was added to 0.5 ml. (6.0 mmol) of concentrated hydrochloric acid in 5.01 ml. of ethanol to give a brown solution with a small amount of a tan insoluble solid. The insolubles were filtered off and the clear solution was added with stirring to 257.7 mg. (1.533 mmol) of 4-fluorophenylglyoxylic acid as prepared in step (a) above.

After 15 minutes of stirring a light yellow solid formed. The solid was filtered off and washed with ethanol and ether. The yield was 294.0 mg. (74%) of the title product; m.p.>300° C.

Analysis: Calc. for $C_{19}H_{12}O_3N_4ClF$: C-57.22; H-3.03; N-14.05%. Found: C-57.05; H-3.32; N-13.88%.

EXAMPLES 3–6

Starting from the 8'-amino derivative of formula (II) and following the procedure of Example 1(c) using the appropriate α-keto acid (source indicated), acid catalysis and reaction time as set out in the following Table 1, the indicated compounds of formula (I) were prepared:

Example 3: 9'-chloro-5',6'-dihydro-2'-ethyl-spiro[imidazolidine-5,7'-7'H-pyrido(1,2,3,-de) quinoxaline]2,3',4-trione.
Example 4: 9'-chloro-5',6'-dihydro-2'-isobutyl-spiro[imidazolidine-5,7'-7'H-pyrido(1,2,3-de) quinoxaline]2,3',4-trione.
Example 5: 9'-chloro-5',6'-dihydro-2'-hexyl-spiro[imidazolidine-5,7'-7'H-pyrido(1,2,3-de) quinoxaline]2,3',4-trione.
Example 6: 9'-chloro-5',6'-dihydro-2'-heptyl-spiro[imidazolidine-5,7'-7'H-pyrido(1,2,3-de) quinoxaline]2,3',4-trione.

EXAMPLE 7

100 mg. (0.37 mmol) of the 8'-amino derivative of formula (II), 60.0 mg. (0.46 mmol) of butylglyoxylate (Pfalty and Bauer), 1.0 ml. (12 mmol) of conc. hydrochloric acid and 3.0 ml. of ethanol were stirred together at room temperature for one hour.

The resulting yellow solid was filtered, washed with ethanol and ether and dried in vacuo at 120° C., to provide 50.54 mg. (49%) of the product 9'-chloro-5',6'-dihydro-spiro[imidazolidine-5,7'-7'H-pyrido (1,2,3-de)-quinoxaline]-2,3',4-trione (Formula I; R=H); m.p.>300° C.

EXAMPLES 8–12

Starting from the 8'-amino derivative of formula (II) and following the procedure of Example 7 using the

TABLE 1

| Example No. | R | -keto Acid (source) | Reaction Catalyst (equiv) | Reaction Time (hr) | mp (°C.) | Yield (%) |
|---|---|---|---|---|---|---|
| 3 | $CH_3CH_2$— | $CH_3CH_2\overset{O}{\underset{\|}{C}}$—COOH (Aldrich) | HCl (20) | 0.3 | 242° dec | 74 |
| 4 | $(CH_3)_2CHCH_2$— | $(CH_3)_2CHCH_2\overset{O}{\underset{\|}{C}}COOH$ (Preparation A) | HCl (6.3) | 1.0 | 253° | 43 |
| 5 | $CH_3(CH_2)_5$— | $CH_3(CH_2)_5\overset{O}{\underset{\|}{-C}}$—COOH (Sigma) | HCl (15) | 1.0 | 219° | 32 |
| 6 | $CH_3(CH_2)_6$— | $CH_3(CH_2)_6\overset{O}{\underset{\|}{C}}$—COOH (Sigma) | HCl (20) | 1.0 | 193° | 39 |

The respective products of Examples 3–6 are as follows:

appropriate α-keto ester (source indicated), acid catalysis and reaction time as set out in the following Table 2, the indicated compounds of Formula (I) were prepared.

TABLE 2

| Example No. | R | -keto ester (source) | Reaction Catalyst (equiv) | Reaction Time (hr) | mp (°C.) | Yield (%) |
|---|---|---|---|---|---|---|
| 8 | $CH_3$— | $CH_3\overset{O}{\underset{\|}{C}}$—$COOC_2H_5$ (Pfalty & Bauer) | HCl (7) | 0.75 (at 85° C.) | 253° | 66 |
| 9 | $(CH_3)_2CH$— | $(CH_3)_2CH\overset{O}{\underset{\|}{-C}}$—$COOC_2H_5$ (Aldrich) | HCl (7) | 2.0 | 219° dec | 24 |

TABLE 2-continued

| Example No. | R | —keto ester (source) | Reaction Catalyst (equiv) | Reaction Time (hr) | mp (°C.) | Yield (%) |
|---|---|---|---|---|---|---|
| 10 | 4-pyridyl | ethyl (pyridin-4-yl)glyoxylate (Preparation B) | $CH_3COOH$ (60) | 1.5 | >300° | 88 |
| 11 | 3-pyridyl | ethyl (pyridin-3-yl)glyoxylate (Preparation C) | $CH_3COOH$ (60) | 1.5 | >300° | 79 |
| 12 | $CH_3CH_2OC(O)-$ | $H_5C_2O-C(O)-C(O)-C(O)-OC_2H_5$ (Aldrich) | HCl (36) | 2.0 | 190° dec | 65 |

The respective products of Examples 8–12 are as follows:

Example 8: 9'-chloro-5',6'-dihydro-2'-methyl-spiro[imidazolidine-5,7'-7'H-pyrido-(1,2,3-de) quinoxaline]2,3',4-trione.

Example 9: 9'-chloro-5',6'-dihydro-2'-isopropyl-spiro[imidazolidine-5,7'-7'H-pyrido-(1,2,3-de) quinoxaline]2,3',4-trione.

Example 10: 9'-chloro-5',6'-dihydro-2'-pyrid-4-yl-spiro[imidazolidine-5,7'-7'H-pyrido-(1,2,3-de) quinoxaline]2,3',4-trione.

Example 11: 9'-chloro-5',6'-dihydro-2'-pyrid-3-yl-spiro[imidazolidine-5,7'-7'H-pyrido-(1,2,3-de) quinoxaline]2,3',4-trione.

Example 12: 9'-chloro-5',6'-dihydro-spiro[imidazolidine-5,7'-7'H-pyrido-(1,2,3-de) quinoxaline]2,3',4-trione-2'-carboxylic acid ethyl ester.

EXAMPLE 13

500 mg. (1.87 mmol) of the 8'-amino derivative of formula II, 350 mg. (2.40 mmol) of fluoropyruvic acid sodium salt (Aldrich), 27 ml. of ethanol and 6.8 ml. of glacial acetic acid were stirred at room temperature for three hours. A small amount of inorganic solids was filtered and the mother liquor was concentrated in vacuo to a brown oil. After removing by azeotrope traces of acetic acid with 4×100 ml of hexane the resultant brown solid was partitioned between ethyl acetate and water 100 ml. each. The organic layer was washed with brine, dried ($MgSO_6$), filtered and evaporated in vacuo to a tan solid; providing 541 mg. (94%) of the product, 9'-chloro-5',6'-dihydro-2'-fluoromethyl-spiro[imidazolidine-5,7'-7'H-pyrido-(1,2,3-de)quinoxaline]-2,3',4-trione (Formula I, $R=FCH_2-$); m.p. 259°–264° C. dec.

EXAMPLES 14–18

Starting from the 8'-amino derivative of formula (II) and following the procedure of Example 13 using the appropriate sodium salt of the α-keto acid (source indicated), acid catalysis and reaction time as set out in Table 3, the indicated compounds of formula (I) were prepared.

TABLE 3

| Example No. | R | —keto acid salt (source) | Acid catalyst (equiv) | Time (hr) | mp (°C.) | Yield (%) |
|---|---|---|---|---|---|---|
| 14 | $CH_3(CH_2)_2-$ | $CH_3(CH_2)_2-C(O)-C(O)-ONa$ (Aldrich) | HCl (11) | 2 | 237° | 18 |
| 15 | $CH_3(CH_2)_3-$ | $CH_3(CH_2)_3-C(O)-CONa$ (Sigma) | HCl (11) | 3 | 259° | 59 |
| 16 | $CH_3-CH_2CH(CH_3)-$ | $CH_3CH_2CH(CH_3)-C(O)-C(O)-ONa$ (Aldrich) | HCl (8) | 16 | >300° | 9 |
| 17 | benzyl ($C_6H_5CH_2-$) | $C_6H_5CH_2-C(O)-C(O)-ONa$ (Chemalog) | HCl (22) | 1 | >300° | 34 |

TABLE 3-continued

| Example No. | R | —keto acid salt (source) | Acid catalyst (equiv) | Time (hr) | mp (°C.) | Yield (%) |
|---|---|---|---|---|---|---|
| 18 | $CH_3S(CH_2)_2-$ | $CH_3S(CH_2)_2-\overset{O}{\underset{\|}{C}}-\overset{O}{\underset{\|}{C}}-ONa$ (Sigma) | HCl (11) | 1 | 231° dec | 7 |

The respective products of Examples 14–18 are as follows:

Example 14: 9'-chloro-5',6'-dihydro-2'-propyl-spiro[imidazolidine-5,7'-7'H-pyrido(1,2,3-de) quinoxaline]2,3',4-trione.

Example 15: 2'-butyl-9'-chloro-5',6'-dihydro-spiro[imidazoline-5,7'-7'H-pyrido(1,2,3-de) quinoxaline]2,3',4-trione.

Example 16: 9'-chloro-5',6'-dihydro-2'-(1-methyl propyl)-spiro[imidazolidine-5,7'-7'H-pyrido(1,2,3-de) quinoxaline]2,3',4-trione.

Example 17: 2'-benzyl-9'-chloro-5',6'-dihydro-spiro[imidazolidine-5,7'-7'H-pyrido(1,2,3-de) quinoxaline]2,3',4-trione.

Example 18: 9'-chloro-5',6'-dihydro-2'-(2-methylthioethyl)-spiro[imidazolidine-5,7'-7'H-pyrido(1,2,3-de)-quinoxaline]2,3',4-trione.

EXAMPLE 19

150 mg. (0.4 mmol) of 9'-chloro-5',6'-dihydro-spiro[imidazolidine-5,7'-7'H-pyrido-(1,2,3-de) quinoxaline]2,3',4-trione-2'-carboxylic acid ethyl ester (formula VI), as prepared in Example 12, was suspended in 3 ml. of cyclohexylamine. The mixture was warmed to effect dissolution then allowed to cool to room temperature and stirred for 30 minutes. The reaction mixture was diluted with 15 ml of 10% HCl and the resulting solid was filtered, washed with water and dried in vacuo; providing 160 mg. (87%) of 9'-chloro-N-cyclohexyl-5',6'-dihydro-spiro[imidazolidine-5,7'-7'H-pyrido-(1,2,3-de) quinoxaline]2,3',4-trione-2'-carboxamide; m.p.>300° C.

EXAMPLES 20–26

Starting from the ethyl ester of formula (VI) prepared by the procedure of Example 12 and following the procedure of Example 19 using the appropriate amine of formula $HNR^1R^2$, temperature and time as set out in the following Table 4, the indicated compounds of formula (VII) were prepared.

TABLE 4

| Example No. | $R = -\overset{O^-}{\underset{\|}{C}}-NR^1R^2$ | amine | Reaction Temperature (°C.) | Reaction Time (hr) | mp (°C.) | Yield (%) |
|---|---|---|---|---|---|---|
| 20 | $CH_3(CH_2)_3NH\overset{O}{\underset{\|}{C}}-$ | $CH_3(CH_2)_3-NH_2$ | 20 | 0.25 | >300 | 84 |
| 21 | $(CH_3)_2N(CH_2)_3-NH\overset{O}{\underset{\|}{C}}-$ | $(CH_3)_2N(CH_2)_3NH_2$ | 20 | 1.0 | 227° dec | 55 |
| 22 | $HO(CH_2)_2NH\overset{O}{\underset{\|}{C}}-$ | $HO(CH_2)_2-NH_2$ | 20 | 1.0 | >300 | 8 (by chromatography) |
| 23 | $(CH_3CH_2)_2N\overset{O}{\underset{\|}{C}}-$ | $(CH_3CH_2)_2NH$ | 20 | 24. | 150° dec | 78 |
| 24 | $NH_2-\overset{O}{\underset{\|}{C}}-$ | $NH_4OH$ | 20 | 0.5 | 300 | 90 |
| 25 | 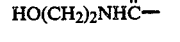 | 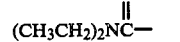 | 20 | 72 | 285° dec | 21 |
| 26 | 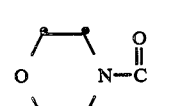 | 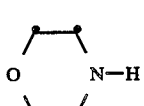 | 20 | 240 | 236° dec | 62 |

The respective products of Examples 20–26 are as follows:

Example 20: N-butyl-9'-chloro-5',6'-dihydro-spiro[imidazolidine-5,7'-7'H-pyrido(1,2,3-de)quinoxaline]-2,3',4-trione-2'-carboxamide.

Example 21: 9'-chloro-5',6'dihydro-N-(3-dimethylaminopropyl)-spiro[imidazolidine-5,7'-7'H-pyrido-(1,2,3-de) quinoxaline]2,3',4-trione-2'-carboxamide.

Example 22: 9'-chloro-5',6'-dihydrO-N-(2-hydroxyethyl)-spiro[imidazolidin-5,7'-7'H-pyrido-(1,2,3-de) quinoxaline]2,3',4-trione-2'-carboxamide.

Example 23: 9'-chloro-N,N-diethyl-5',6'-dihydro-spiro[imidazolidine-5',7-7'H-pyrido-(1,2,3-de) quinoxaline]2,3',4-trione-2'-carboxamide.

Example 24: 9'-chloro-5',6'-dihydro-spiro[imidazolidine-5',7-7'H-pyrido(1,2,3-de) quinoxaline]2,3',4-trione-2'-carboxamide.

Example 25: 9'-chloro-5',6'-dihydro-spiro[imidazolidine-5',7-7'H-pyrido(1,2,3-de) quinoxaline]2,3',4-trione-2'-carboxylic acid, pyrrolidine amide.

Example 26: 9'-chloro-5',6'-dihydro-spiro[imidazolidine-5',7-7'H-pyrido(1,2,3-de) quinoxaline]2,3',4-trione-2'-carboxylic acid morpholine amide.

The preparation of the starting α-keto acid for the compound of Example 4 and the preparation of the starting α-keto esters for the compounds of Examples 10 and 11 are illustrated in the following Preparations A, B and C, respectively.

PREPARATION A 5-keto-isocaproic acid 1.00 g. (7.57 mmol) of 5-hydroxy isocaproic acid was oxidized with 0.82 g. (5.22 mmol) of potassium permanganate in an aqueous base according to the procedure of Carson, et al., Org. Syn. Col. Vol. 1, 241 (1941). The oily product contaminated with a minor amount of starting material was characterized by NMR and used without further purification.

PREPARATION B 4-pyridyl glyoxylic acid 15.0 g. (0.095 mol) of 4-bromopyridine in 7 ml. of dry tetrahydrofuran (THF) was added dropwise at −70° C. to a solution of butyl lithium (1.6 M, 60.9 ml., 0.098 mol) dissolved in 120 ml. of dried THF over a ten minute period. The resulting very deep purple mixture was stirred at −70° C. for 30 minutes and then transferred by nylon tubing under positive nitrogen pressure into a stirred 0° C. solution of ethyl oxalate (55.2 g., 0.38 moles) in 90 ml. of dry THF. The solution was stirred at 0° C. for 45 minutes and then quenched by addition of 65 ml. glacial acetic acid. This was warmed to room temperature and poured into 500 ml. of water adjusted to pH 7.0 with saturated sodium bicarbonate and extracted with 3×200 ml. ethyl acetate. The combined organic layers were washed with brine, dried over magnesium sulfate filtered and concentrated to a brown oil. This oil was flash chromatographed on silica gel eluted with 1:2 ethyl acetate hexane. A viscous yellow oil was obtained; 5.8 g (34%), m/e 179, spectral data consistent with structure of title product.

PREPARATION C 3-pyridyl glyoxylic acid 10 g. (0.063 mol) of 3-bromopyridine in 80 ml. of dry THF was added dropwise to a −70° C. solution of butyl lithium (1.6M, 40.6 ml, 0.065 mol) dissolved in 120 ml. of dried THF over a 20 minute period. The resulting brown solution was stirred at −70° C. for 30 minutes and then transferred by nylon tubing under positive nitrogen pressure into a stirred 0° C. solution of ethyl oxalate (36.8 g, 0.25 mol) in 60 ml of dry THF. The solution was stirred at 0° C. for 45 minutes, quenched by addition of 50 ml. glacial acetic acid, warmed to room temperature and poured into 500 ml of water, adjusted to pH 7.0 with 750 ml saturated sodium bicarbonate and extracted with 2×500 ml ethyl acetate. The combined organic layers were washed with brine, dried (MgSO4), filtered and concentrated in vacuo to a brown oil; 24.7 g. This oil was flash chromatographed on silica gel eluted with 1:2 ethyl acetate hexane. A viscous yellow oil was obtained; 1.56 g, m/e 179, spectral data consistent with structure of title product.

I claim:

1. A biologically-active tetracyclic spiro hydantoin derivative having the general formula:

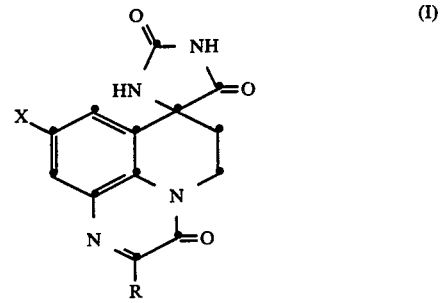

and the pharmaceutically-acceptable acid addition salts thereof; wherein

X is hydrogen, fluorine, chlorine or methyl; and R is hydrogen, (C1-C9)alkyl, (C2-C9)alkenyl, (C5-C7-)cycloalkyl, benzyl, 4-hydroxybenzyl, pyridyl, HSCH2—, CH3SCH2—, CH3SCH2CH2—, FCH2—, HOCH2—, CH3CH(OH)—, CH3CH(OH)CH2—, HOOCCH2—, HOOCCH2CH2—, H2NCOCH2—, H2NCOCH2CH2—, H2NCH2CH2CH2CH2—,

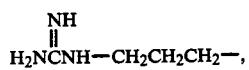

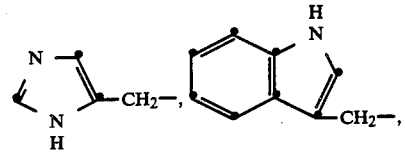

—COOC2H5, —CONH2, —CONH(CH2)2OH, —CONH cyclohexyl, —CONH-nBu, —CONH(CH2)3 N(CH3)2, —CON(C2H5)2,

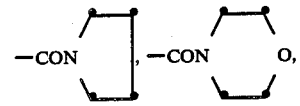

phenyl or substituted phenyl wherein the substituent is chlorine, fluorine, bromine, hydroxy, methyl, methoxy, trifluoromethyl, —COCH3, —N(CH3)2, —SCH3, —SOCH3, —SO2CH3, —COOH, —CONH2, —COOCH3 or —CON Alk, wherein Alk is lower alkyl having 1 to 6 carbon atoms.

2. A compound according to claim 1, in which X is chlorine.

3. A compound according to claim 2, in which R is phenyl.

4. A compound according to claim 2, in which R is —CONR1R2 wherein R1 and R2 are both hydrogen or ethyl or R1 is hydrogen and R2 is n-butyl, cyclohexyl, dimethylaminopropyl or 2-hydroxethyl; or R1 and R2 together with the nitrogen atom to which they are attached form a pyrrolidino or morpholino ring.

5. A pharmaceutical composition for the treatment of diabetes complications comprising a pharmaceutically effective amount of a compound according to claim 1 in admixture with a pharmaceutically-acceptable carrier.

* * * * *